(12) United States Patent
Mullen

(10) Patent No.: US 6,533,492 B2
(45) Date of Patent: Mar. 18, 2003

(54) JOINTS FOR METALLIC MEMBERS AND STRUCTURES FORMED USING THE SAME

(76) Inventor: Stephen J. Mullen, 2 Conifer Way, Beverly, MA (US) 01915

( * ) Notice: Subject to any disclaimer, the term of this patent is extended or adjusted under 35 U.S.C. 154(b) by 28 days.

(21) Appl. No.: 09/825,099

(22) Filed: Apr. 3, 2001

(65) Prior Publication Data

US 2001/0043834 A1 Nov. 22, 2001

Related U.S. Application Data

(60) Provisional application No. 60/194,081, filed on Apr. 3, 2000.

(51) Int. Cl.[7] ............................................. F16C 13/00
(52) U.S. Cl. ......................................... 403/268; 492/58
(58) Field of Search ................................. 403/268, 265; 156/222; 425/80.1

(56) References Cited

U.S. PATENT DOCUMENTS

| | | | | |
|---|---|---|---|---|
| 4,695,422 A | * | 9/1987 | Curro et al. ................. | 264/504 |
| 4,878,825 A | * | 11/1989 | Mullane, Jr. ................ | 425/290 |
| 6,146,580 A | * | 11/2000 | Bontaites, Jr. .............. | 264/555 |
| 6,312,640 B1 | * | 11/2001 | Shimalla ..................... | 264/504 |

* cited by examiner

*Primary Examiner*—Robert J. Sandy
(74) *Attorney, Agent, or Firm*—Grossman, Tucker, Perreault & Pfleger, PLLC

(57) ABSTRACT

A joint for metallic members including a body portion and extending portion in one member and an opening in a second member. The body portion of one member at least partially overlaps the opening in the second member to create a joined opening. A bonding agent, e.g. adhesive, is applied in the joined opening to create a strong joint relying on the sheer strength of the cured bonding agent rather than its peel strength. Slot-to-slot and tab-to-slot joints using joined openings are provided. A drum and mechanical structure constructed using laser cutting techniques on metallic plates and utilizing the disclosed joints are also provided.

10 Claims, 11 Drawing Sheets

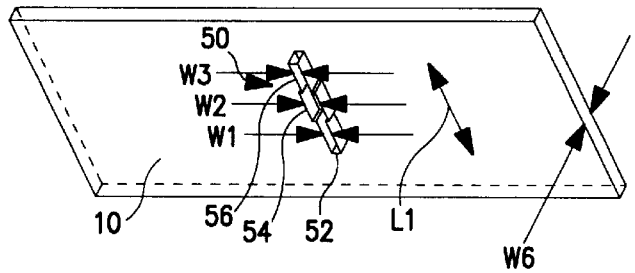 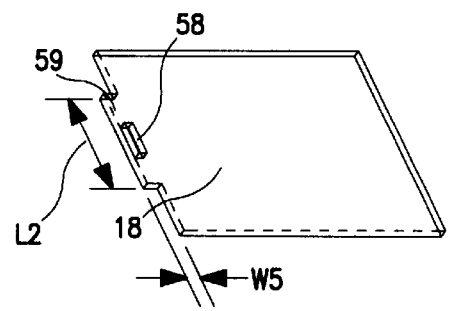
FIG. 5A    FIG. 5B
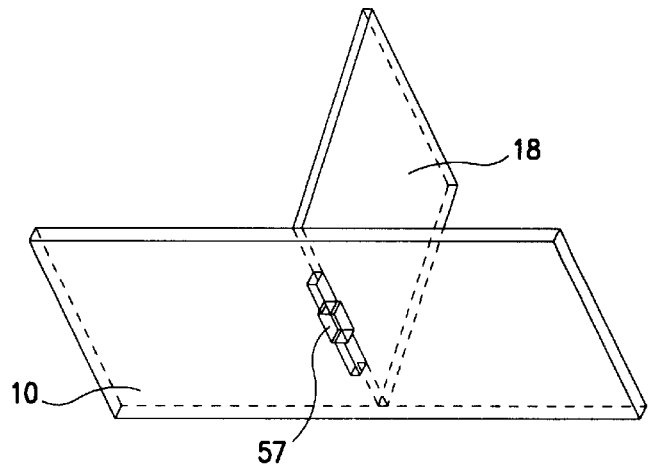
FIG. 5C

JOINTS FOR METALLIC MEMBERS AND STRUCTURES FORMED USING THE SAME

CROSS-REFERENCE TO RELATED APPLICATIONS

The present application claims the benefit of the filing date of U.S. Provisional Application No. 60/194,081 filed Apr. 3, 2000, the teachings of which are incorporated herein by reference.

FIELD OF THE INVENTION

The present invention relates generally to joints formed in metal parts and to structures formed using the same.

BACKGROUND OF THE INVENTION

A commonly used method of providing high strength and lightweight characteristics is to construct a structure using a cellular web extending between respective plates. The web may be typically honeycomb shaped with each honeycomb cell having a hexagonal shape. The honeycomb shapes may be formed of corrugated metal strips laterally displaced from one another and joined to have the appearance of natural honeycomb. The web is usually welded, brazed, or otherwise fastened to the face sheets.

The applications for these types of honeycomb structures are numerous. A main difficulty with the structures, however, is that they are cumbersome and inefficient to manufacture. For example, a honeycomb drum for use in the non-woven industry, e.g. to make baby diapers, has been formed using heavy aluminum castings which must be extensively machined. Framed honeycomb segments composed of cells of classic six-sided honeycomb are bolted to the machined castings and the outer diameter surface of the honeycomb is machined. A micro-etched screen is welded to the exposed outer honeycomb surface to create the desired vacuum-forming surface. The drum typically includes ribs traversing its width that may be as much 0.150"–0.200" thick in a typical drum of about 2' diameter to support loads imposed upon the drum. Because of this, the drum may weigh as much as 250 lbs., making it cumbersome for handlers.

Accordingly, there is a need in the art for lightweight cell structure that may be constructed by simple fabrication techniques.

SUMMARY OF THE INVENTION

A joint consistent with the present invention includes a first metallic member with a first opening having a body portion and extending portion. A second metallic member having a second opening is disposed in the first opening of the first member so that the second opening at least partially overlaps the body portion to create a joined opening. A bonding agent, e.g. adhesive, is applied in the joined opening so that when cured, it forms an integral part of the joint.

A slot-to-slot joint consistent with the invention includes each metallic member equipped with a slot. Each slot has a body portion and extending portion. The two members are slid together so that their respective body portions at least partially overlap to define a joined area where a boding agent may be applied. Alternatively, each member may be additionally equipped with a cutout aligned with each slot so that the cutout from the first member at least partially aligns with the body portion from the second member and vice versa.

A tab-to-slot joint consistent with the present invention includes a first metallic member with a tab having a cutout at least partially disposed within the tab. A second member has a slot that includes a body portion and extending portion. The tab of the first member is inserted into the slot of the second member so that the cutout at least partially overlaps the body portion to define a joined opening where bonding agent may be applied.

A drum laser cut from metallic sheets includes a plurality of annular members joined by a plurality of ribs via different joints such as slot-to-slot and tab-to-slot joints. A mechanical housing includes a cell structure sandwiched between first and second metallic plates. Methods of forming joints are also disclosed.

BRIEF DESCRIPTION OF THE DRAWINGS

Advantages of the present invention will be apparent from the following detailed description of exemplary embodiments thereof, which description should be considered in conjunction with the accompanying drawings, in which:

FIGS. 5A–5C are perspective views of a slotted and tabbed plate illustrating an exemplary tab-to-slot connection consistent with the present invention;

DETAILED DESCRIPTION

Figure 1:
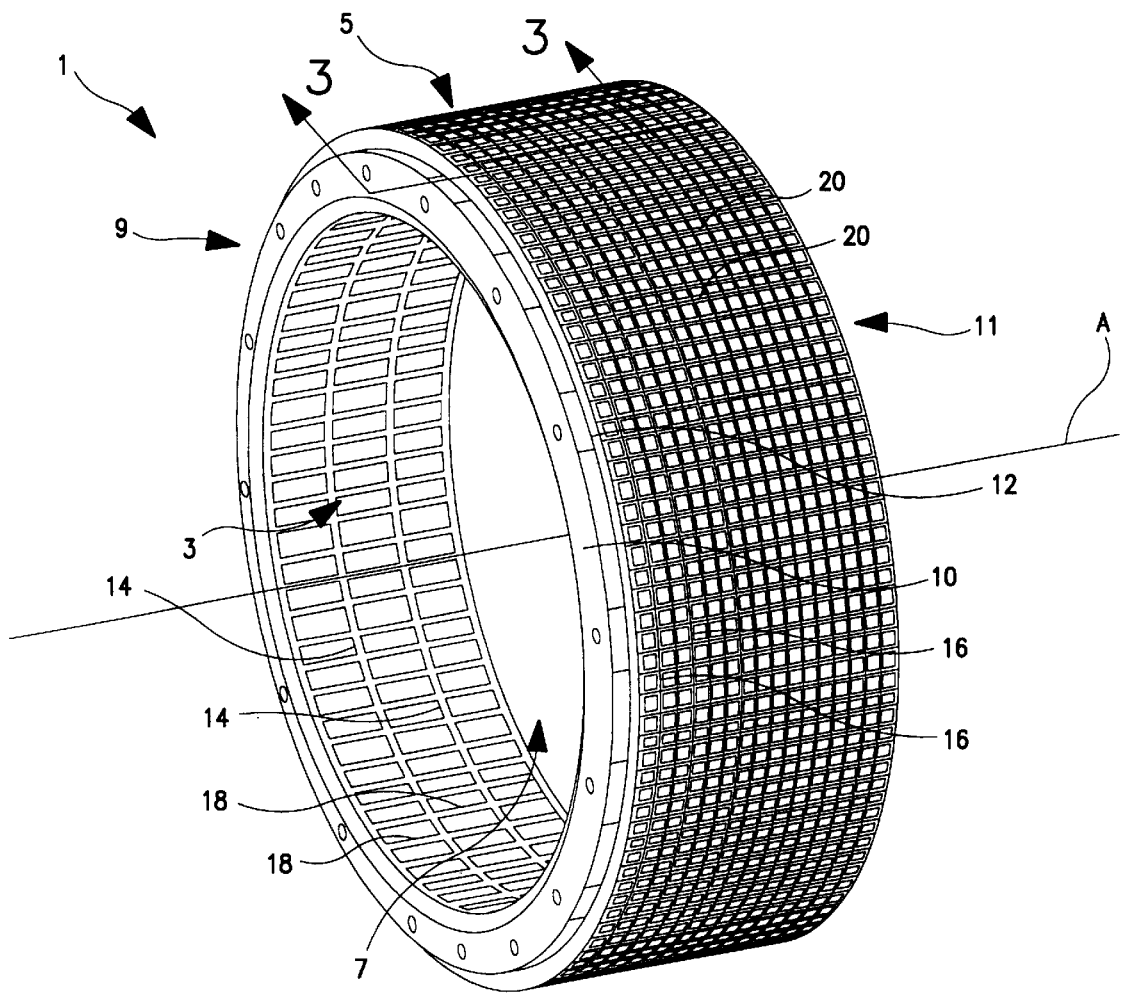
FIG. 1 is a perspective view of an exemplary drum consistent with the present invention.

Referring to FIG. 1, there is shown an exemplary flow through drum consistent with the present invention. The drum 1 includes an interior surface 3 that defines a large aperture 7 and an exterior surface 5.

The exemplary drum 1 is generally comprised of four annular slotted plates, the A-plate 10, B-plate 12, C-plate 14, and D-plate 16, which are coupled via a plurality of primary slotted ribs 18 and secondary slotted ribs 20 arranged orthogonal to the annular plates and generally parallel with the axis of rotation A. The connections between the ribs and the plates are either slot-to-slot connections or tab-to-slot connections.

Generally, rib connections to the outermost plates are tab-to-slot connections while rib connections to the inner plates are slot-to-slot connections. More particularly, the primary rib 18 may be connected to the C-plate 14 via a slot-to-slot connection, to the B-plate 12 via a tab-to-slot connection, and to the A-plate 10 via a tab-to-slot connection. Similarly, the secondary rib 20 may be connected to the D-plate via a slot-to-slot connection, and to the B-plate 12 via a tab-to-slot connection.

Figure 2:
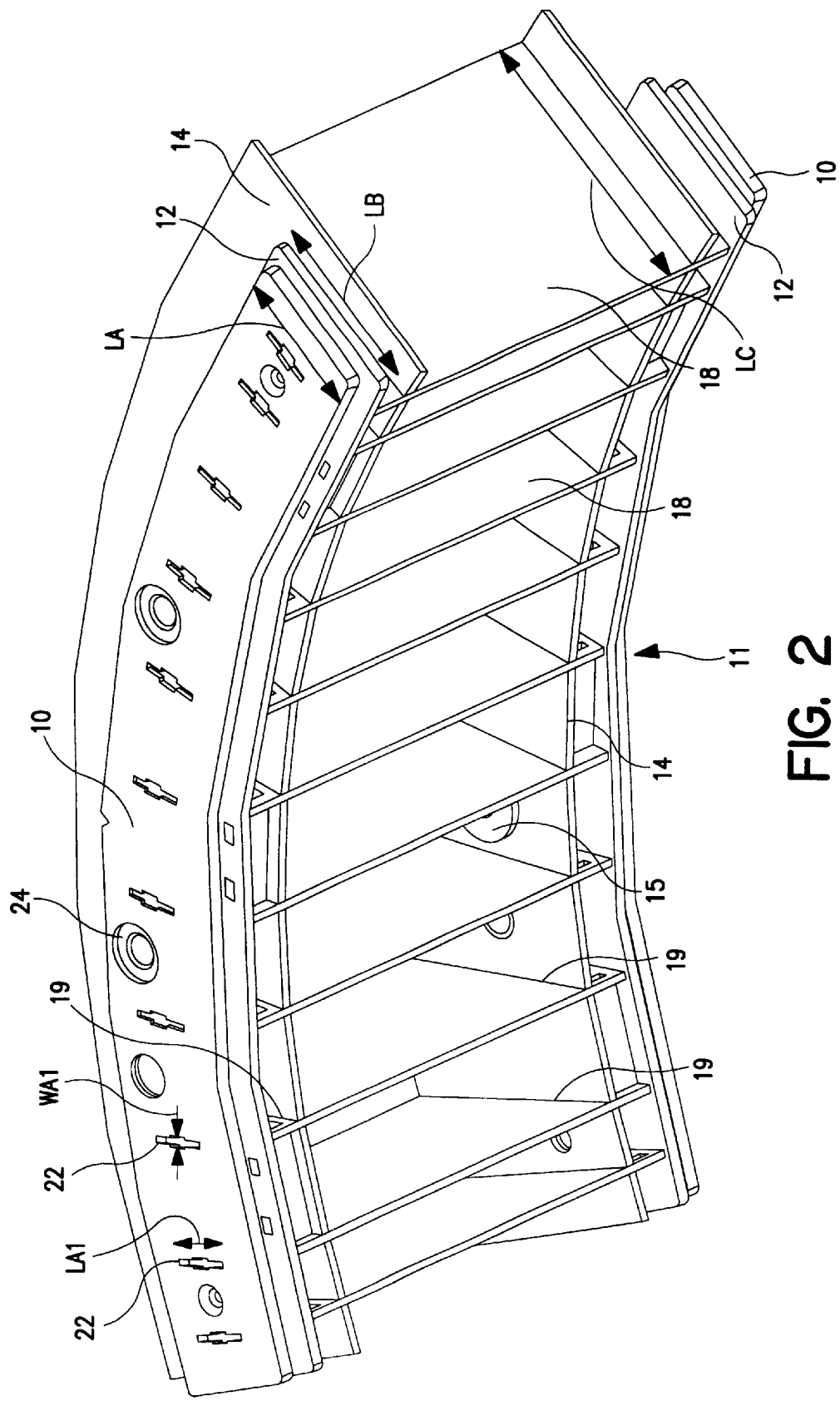
FIG. 2 is an interior perspective view of a portion of the exemplary drum of FIG. 1.

Turning to FIG. 2, a cut away perspective view of the interior side 3 of the exemplary drum 1 of FIG. 1 is illustrated to show the relationship between the various plates and ribs. As illustrated, the A-plate 10 is the outermost annular plate having a radial length LA slightly less than the radial length LB of the B-plate 12. The A-plate is the outermost plate on both the first side 9 and second side 11 of the drum 1. The A-plate may include a plurality of slots 22 having a radial length LA1 and width WA1 to accept the narrower tab 61 (FIG. 6) of the primary rib 18 in a tab-to-slot connection. The A-plate 10 may also be equipped with a plurality of holes 24 for accepting bolts or other such fastening means to affix the A-plate to the C-plate 14, which may include a nut for receiving both.

The B-plate 12 is the next outermost plate on both the first 9 and second ends 11 of the drum 1. The B-plate may also be equipped with a plurality of slots having a radial length longer than the radial length LA1 of the A-plate slots for accepting the wider slot end 63 (FIG. 6) of the primary ribs 18 in a tab-to-slot connection.

The C-plate 14 is an interior annular plate. Generally, the radial length LC of the C-plate 14 is greater than the radial length of the A-plate LA and B-plate LB. In the exemplary drum 1, there are two C-plates 14, which are coupled to a plurality of generally rectangular shaped primary ribs 18 via slot-to-slot connections 19. The ends of the primary ribs are also joined to the A-plates 10 and B-plates 12 on the first 9 and second 11 end of the drum via tab-to-slot connections. Hence, the A-plate 10, the B-plate 12, and the C-plate 14 are all coupled to the plurality of primary ribs 18. It should be understood by those skilled in the art that there may be any number of plates and ribs based on the particulars of the desired application without departing from the scope of the present invention.

Figure 3:
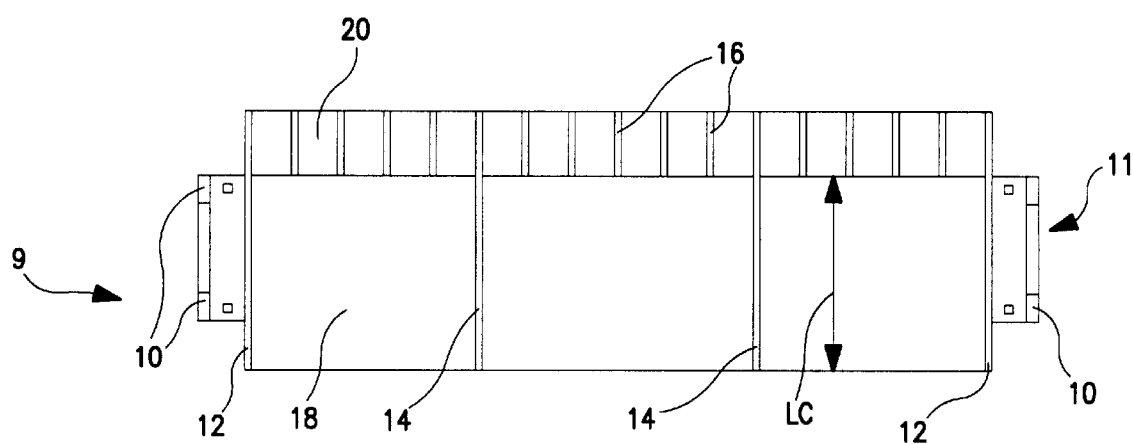
FIG. 3 is a cross-sectional line view taken along the line 3—3 of FIG. 1.

Turning to FIG. 3, a cross sectional view of the exemplary drum taken along the line 3—3 of FIG. 1 is illustrated. A primary rib 18 is connected to two interior C-plates 14 via slot-to-slot joints. Both sides of the primary rib 18 include a wide and narrow tab structure for connecting to the outer B-plates 12 and A-plates 10 respectively via tab-to-slot connection. A plurality of D-plates 16 are disposed above the primary rib 18 and engage secondary ribs 20 via slot-to-slot joints.

Figure 4A:
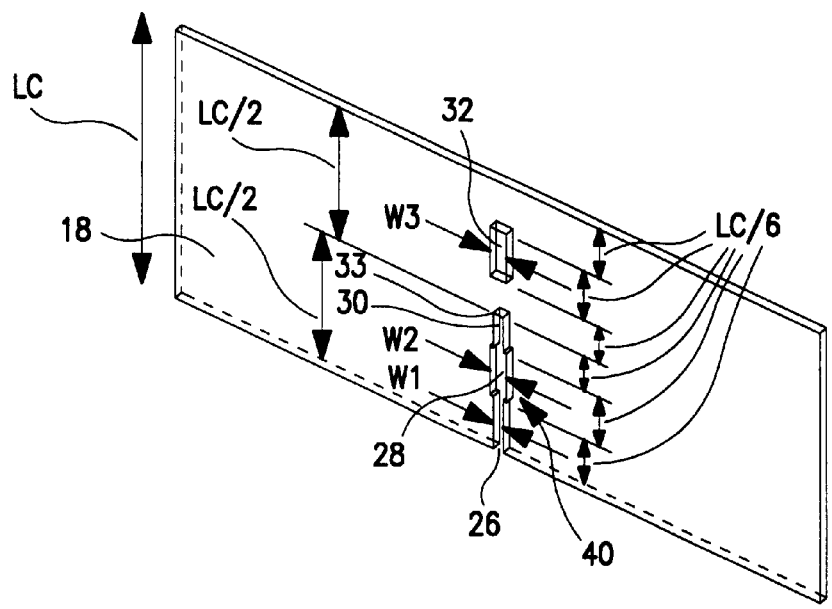
FIGS. 4A and 4B are perspective views of slotted plates illustrating an exemplary slot-to-slot connection consistent with the present invention.
Figure 4B:
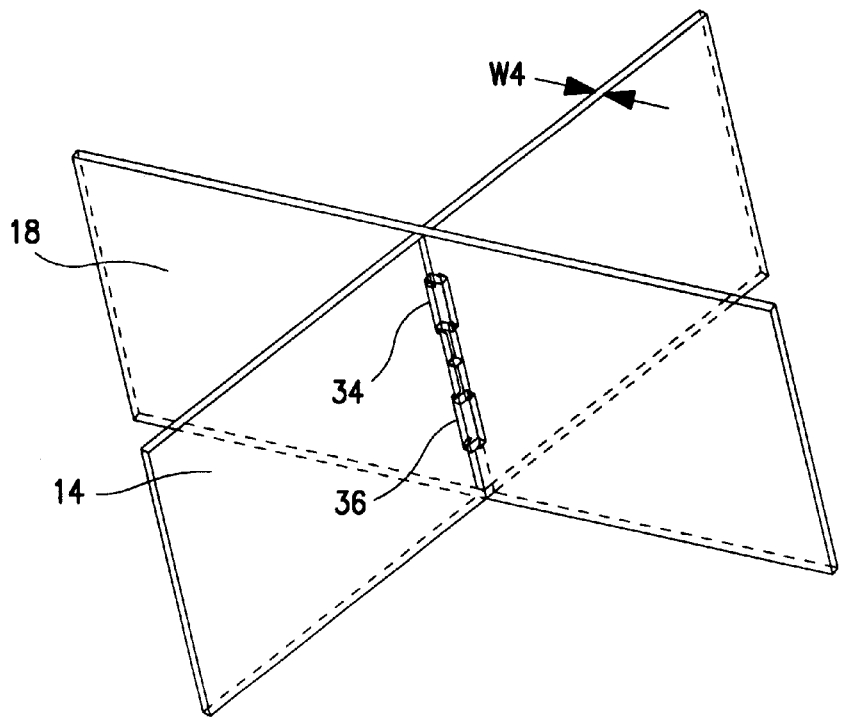
Figure 8:
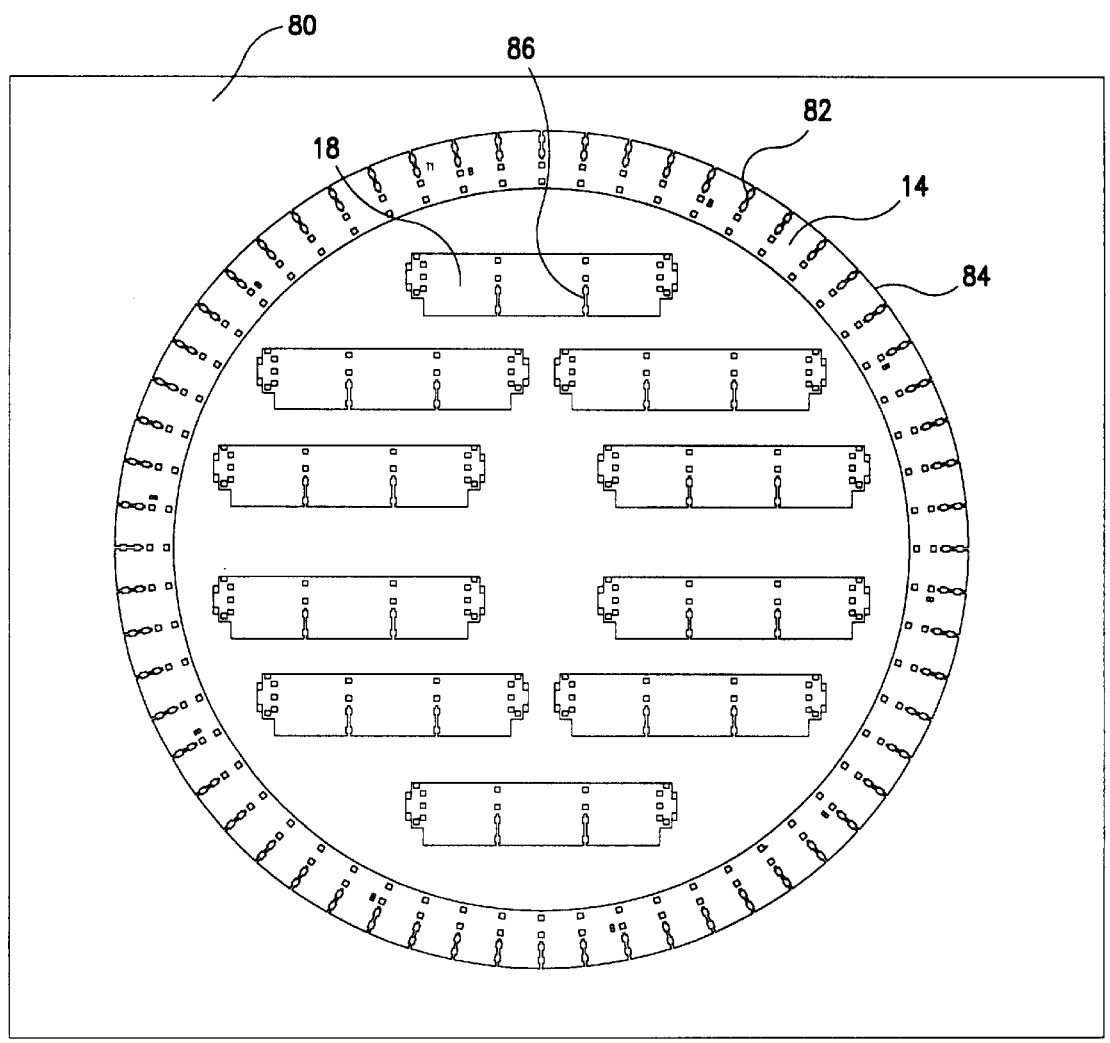
FIG. 8 is a plan view of an exemplary third annular C-plate with radial slots for accepting primary rib members in a slot-to-slot connection.

Turning to FIGS. 4A and 4B, an exemplary slot-to-slot joint is illustrated. Only a piece of each member to be joined is illustrated for clarity. The representative members to be joined are the primary rib 18 and the C-plate 14. Since only a small section of the C-plate is shown for ease of reference, it is shaped generally rectangular as opposed to the true annular C-plate shape as illustrated in FIGS. 1 & 8. Alternatively, the secondary rib 22 and the D-plate 16 may also be joined in similar fashion. Those skilled in the art will recognize that a host of other varying members may be joined using the exemplary slot-to-slot configuration illustrated in FIGS. 4A–4B without departing from the spirit and scope of the present invention.

A slot 40 may be cut using laser sheet cutting technology in the primary rib 18. Laser sheet cutting of metallic parts is a conventional technology.

The slot 40 comprises a first narrow extending section 26, a second wider body section 28, and a third narrow extending section 30 of substantially equal dimensions as the first section 26. The first section may have a width W1 substantially equal to the width W4 of the C-plate 16 to be coupled thereto.

The width W2 of the second body section 28 is greater than the width of the first extending section 26. A cutout 32 has a width W3 that may be substantially similar to the width W2 of the second body section 28. The length of the first extending section 26, second body section 28, third extending section 30, and the cutout 32 may all be substantially equal to LC/6.

Turning to FIG. 4B, the primary rib 18 and C-plate 14 are aligned at right angles to each other and the primary rib 18 is inserted into the C-plate using this slot-to-slot configuration. The C-plate has a slot and cutout structure to match the earlier structure described with reference to the primary rib 18. The primary rib may be inserted into the C-plate 16 until the uppermost portion 33 of the third slot section 30 abuts with the same corresponding section of the C-plate slot.

As such, the cut out 32 of the primary rib 18 is juxtaposed with the second body section 28 of the C-plate 16 at right angles to each other to form a cross-shaped open area 34. Similarly, the second body section 28 of the primary rib 18 is juxtaposed with the cutout 32 of the C-plate 16 at right angles to each other to form a second cross-shaped open area 36. Each of the cross-shaped open areas 34, 36 have four extensions with a length substantially equal to LC/6, a width substantially equal to the difference between W2 and W1, and a thickness substantially equal to W4.

Advantageously, each of these two cross-shaped open areas 34, 36 permits a bonding agent to be inserted thereto. Those skilled in the art will recognize adhesive may be utilized as such bonding agent or any number of materials may be soldered to act as the bonding agent. When allowed to dry or cure, the bonding agent acts as an integral part of the joined members. As such, the resulting slot-to-slot joint relies upon the generally higher shear strength of the bonding agent as opposed to generally lower peel strength.

Figure 6:
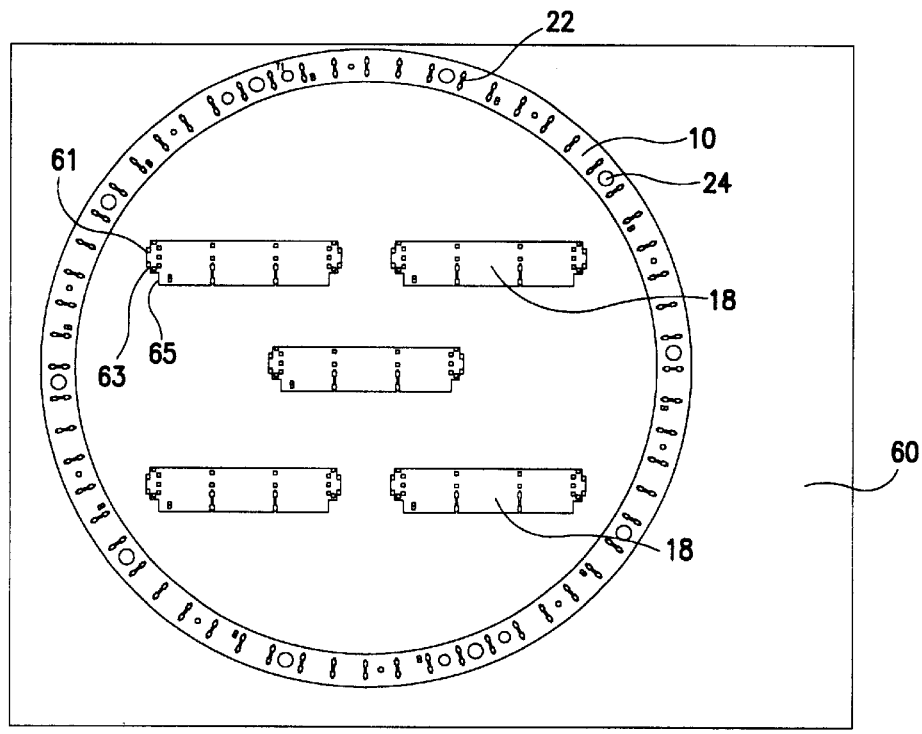
FIG. 6 is a plan view of an exemplary first annular A-plate with one set of radial slots for accepting primary rib members in a tab-to-slot connection.

Turning to FIGS. 5A–5C, an exemplary tab-to-slot joint that also creates an open area for bonding agent to be applied is illustrated. The tab-to-slot connection may be used to join primary ribs 18 and secondary ribs 20 to outermost plates such as A-plates 10 and B-plates 12. The illustrated members to be joined in FIGS. 5A–5C are the A-plate 10 and the primary rib 18. Only a small section of the A-plate is shown for ease of reference and hence it is shaped generally rectangular as opposed to the true annular A-plate shape as illustrated in FIGS. 1 & 6. Those skilled in the art will recognize that a host of other members may be joined using the exemplary tab-to-slot configuration illustrated in FIGS. 5A–5C without departing from the spirit and scope of the present invention.

FIG. 5A illustrates a slot 50 having a first extending portion 52, a second body portion 54, and third extending portion 56 slot with respective widths W1, W2, and W3. The length L1 of the slot 50 may be substantially equal to the length L2 of the tab 59 so that the tab securely fits in the slot. The width W5 of the tab 59 may also be substantially equal to the width W6 of the A-plate 10 so that the tab 59 is flush with the A-plate 10 after insertion. The tab 59 may also be equipped with a cutout 58. The length of the cutout 58 on the primary rib 18 may be substantially equal to the length of the second body portion 54 on the A-plate 10.

Turning to FIG. 5C, the primary rib 18 may be orientated at a right angle to the A-plate 10 so that the tab 59 may be coupled to the slot 50. The coupling of the tab into the slot results in the cutout 58 being juxtaposed with the second body portion 54 of the slot 50 at right angles to each other to form a cross-shaped open area 57. The cross-shaped open area 57 has four extensions with a length substantially equal to L1/3, a width substantially equal to the difference between W2 and W1, and a thickness substantially equal to W6. Those skilled in the art will recognize that a plurality of open areas with varying geometries and dimensions may be employed in a slot-to-slot connection or tab-to-slot connection without departing from the scope and spirit of the present invention. Although the width of the slots may also vary, the laser cutting function can permit the width of the slots to be as narrow as 0.06 inches.

Advantageously, the cross-shaped open area 57 permits a bonding agent to be inserted thereto and allowed to cure. The cured bonding agent then acts as an integral part of the joined members. As such, the resulting tab-to-slot joint relies upon the generally higher shear strength of the cured bonding agent as opposed to generally lower peel strength.

Turning to FIG. 6, the A-plate 10 may be cut from a sheet of material 60. The A-plate 10 may have a plurality of radial slots 22 for accepting the narrower tabbed ends 61 of a plurality of primary ribs 18. The A-plate may also have apertures 24 for accepting bolts or other such fastening means to attach the C-plate to the A-plate. Primary ribs 18 may be cut from the mid area of the sheet 60 or another separate sheet. The primary ribs may also have a wider tab portion 63. The wider tab 63 accepts the B-plate 12 up against the abutting edge 65 of the wider tab 63.

Figure 7:
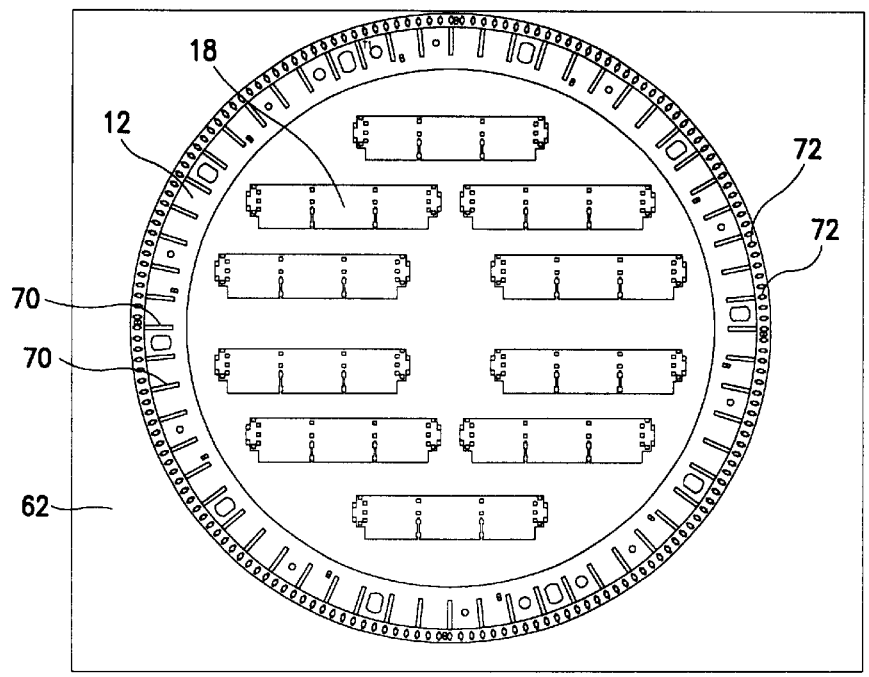
FIG. 7 is a plan view of an exemplary second annular B-plate with two sets of radial slots for accepting primary and secondary rib members in tab-to-slot connections.

Turning to FIG. 7, the annular B-plate 12 may be cut from a sheet 62, and primary ribs 18 may be cut from the center of the sheet. The B-plate 12 may have a first set of radial slots 70 and a second set of concentric radial slots 72. The first set of interior slots 70 may be sized to accept the wider tab 63 from the primary ribs 18. The second set of exterior slots 72 may be sized to accept tabs from the smaller secondary ribs 20. The secondary ribs 20 form a cell structure with the D-plates 16 as described more fully with reference to FIG. 10 and illustrated generally in FIG. 1.

Turning to FIG. 8, the annular C-plate 14 may be cut from a sheet 80 and primary ribs 18 may be cut from the center of the sheet. A plurality of radial slots 82 may be cut in the C-plate 14 to present openings along the outside circumference 84 of the C-plate. The radial slots 82 may be sized to accept the slots 86 cut into the primary ribs 18 for establishing a slot-to-slot connection between the C-plate and the primary ribs 18. The slot-to-slot connection may also be as described earlier with reference to FIGS. 4A & 4B.

Figure 9:
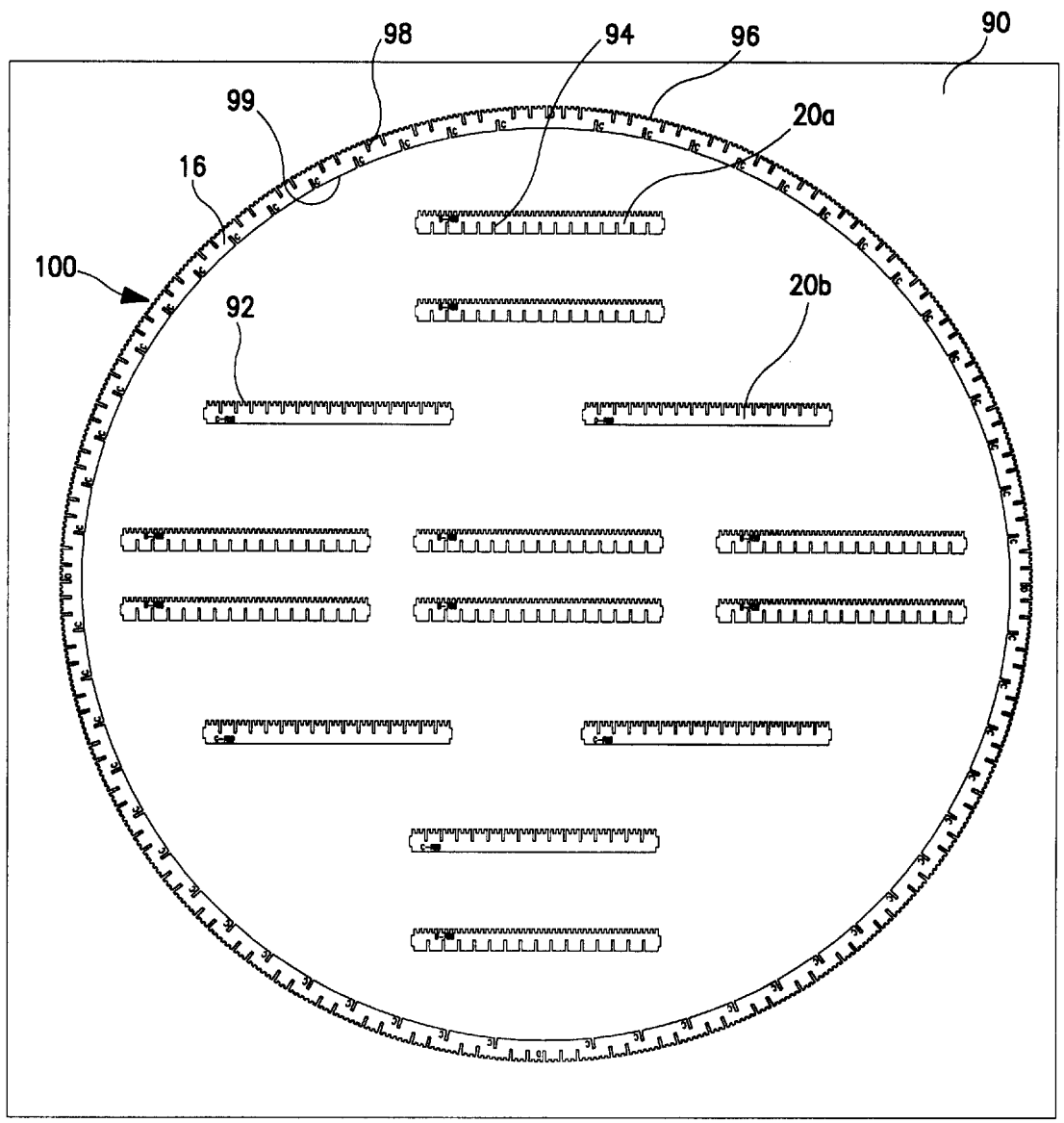
FIG. 9 is a plan view of an exemplary fourth annular D-plate with radial slots for accepting secondary rib members in a slot-to-slot connection.

Turning to FIG. 9, the annular D-plate 16 may be cut from a sheet 90 and secondary ribs 20 may be cut from the center of the sheet. The D-plate may be cut with a plurality of radial slots 98. The radial slots 98 may be arranged in an alternating pattern having two radial slot openings on the outside circumference 96 of the D-plate followed by a radial slot opening on the inside circumference 99.

The secondary ribs may include secondary B ribs 20a and secondary C ribs 20b each having a plurality of slots 94 sized to engage corresponding radial slots 98 of the D-plate in a slot-to-slot configuration. The secondary B-ribs 20a couple to the D-plate via insertion over the outer circumference 96 while the secondary C ribs 20b couple to the D-plate via insertion by the inner circumference 99.

Figure 10:
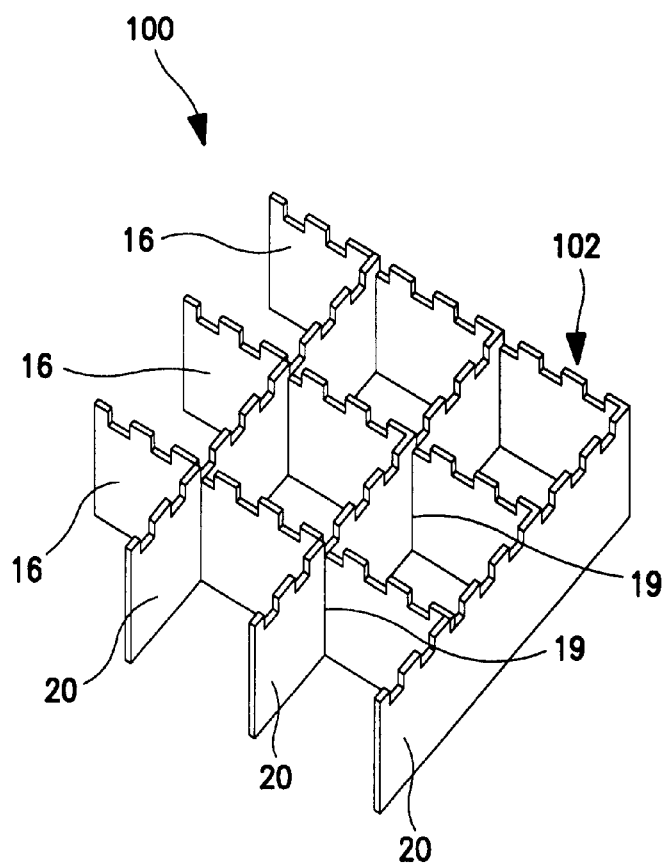
FIG. 10 is an elevation view of a cellular support structure.
Figure 11:
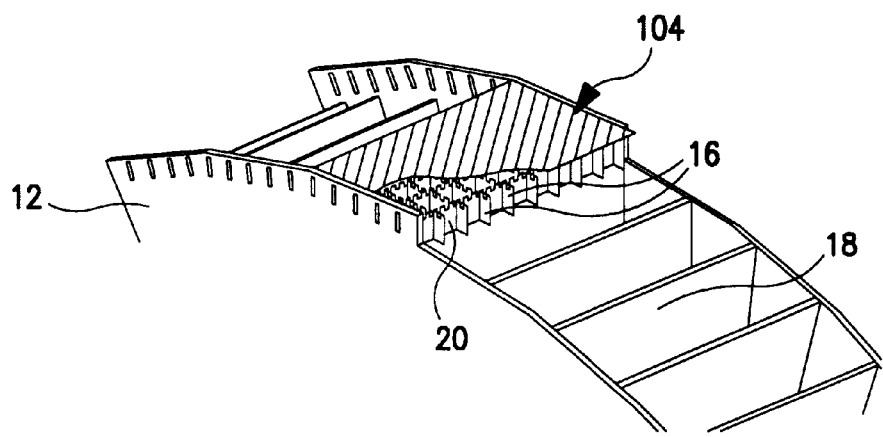
FIG. 11 is a cut away perspective view illustrating connection of a screen to the scalloped edge cellular support structure of FIG. 10.

Turning to FIG. 10, a small section of a modified cell structure 100 is illustrated. The cell structure 100 is comprised of pieces of the annular D-plates 16 and secondary ribs 20, each having scalloped edges 102, connected via slot-to-slot joints 19. A screen 104 may be affixed to the scalloped edges as can be best seen in FIG. 11. The screen may be resistance welded to the scalloped edges. In this instance, the cell structure that is snapped together utilizing a slot-to-slot joint would not require any bonding agent to be used in the slot-to-slot joints. The scalloped edges 102 maximize the open area between the cellular structure 100 and the screen 104.

Figure 12:
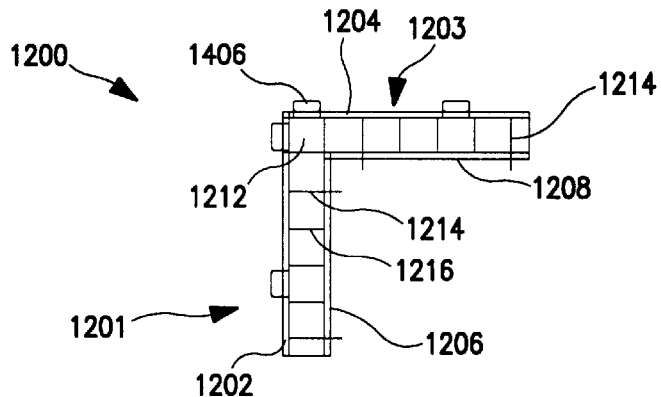
FIG. 12 is a cross section view of a second embodiment of the present invention.

Turning to FIG. 12, a second embodiment consistent with the present invention is illustrated. The second embodiment is a housing 1200 made up of a plurality of sandwiched structures with brazed joints, where each structure may include an exterior plate and an interior plate sandwiching a plurality of ribs. Such housing structures are strong and lightweight and may be utilized in the aircraft industry to enclose sensitive equipment, e.g. electronic equipment. Those skilled in the art will also recognize that a single sandwiched structure may be utilized to form various support structures used in a variety of applications, e.g. floors and wall support in aircraft.

A perspective cross sectional view of one corner of an exemplary housing 1200 is illustrated in FIG. 12. One wall 1201 is joined to a ceiling 1203 at a corner. Similarly, a plurality of different walls, ceilings, and floors may be joined at different corners to create an enclosed housing. The wall 1201 may include an exterior wall plate 1202 connected to an interior wall plate 1206 via a plurality of ribs. Similarly, the ceiling 1203 may include an exterior ceiling plate 1204 connected to an interior ceiling plate 1208 via a plurality of ribs. Advantageously, the exterior ceiling plate 1204 includes a plurality of notches 1302 to accept corresponding tabs 1304 from the exterior wall plate 1202 to form an integrated exterior edge. Similarly, the interior ceiling plate 1208 includes a plurality of notches 1306 to accept corresponding tabs 1308 from the interior wall plate 1206.

Turning to FIGS. 14A–14D and FIG. 15, the plurality of ribs and an exemplary cell configuration of ribs that may be sandwiched between the exterior and interior plates is illustrated. For ease of explanation, the plurality of ribs includes a set of vertical ribs 1502 and horizontal ribs 1504 with respect to the plates of FIGS. 13A–13D. The set of vertical ribs 1502 includes a standard vertical rib 1212 and a tabbed vertical rib 1210, while the horizontal ribs 1504 includes a standard horizontal rib 1216 and a tabbed horizontal rib 1214. Due to laser cutting, the ribs may be only 0.006 inches thick aluminum in this embodiment and the exterior and interior plates may be 0.063 inches thick aluminum.

Figure 13B:
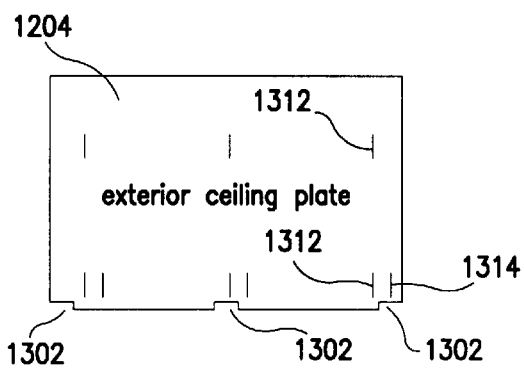
FIGS. 13A–13D are plan views of exemplary plates for use in the second embodiment of FIG. 12.
Figure 13D:
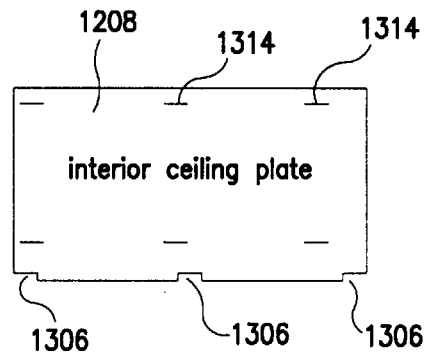
Figure 13A:
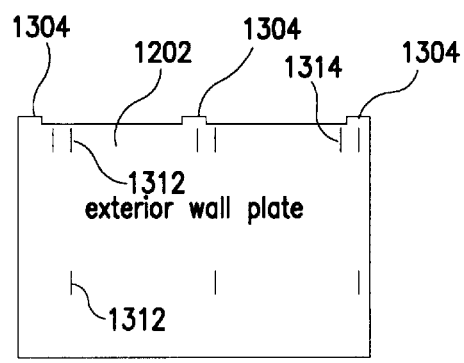
Figure 13C:
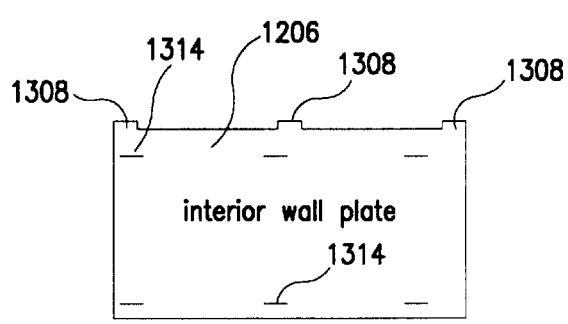

The slots 1404 of the standard vertical rib 1212 engage corresponding slots 1410 of the horizontal ribs 1214, 1216. One set of tabs 1402 of the tabbed vertical rib 1210 protrude at right angles with respect to the length of the rib. These right angle tabs 1402 engage corresponding slots 1312 in the exterior plates 1202, 1204 (FIGS. 13A–13B). The other tab 1406 of the tabbed vertical rib 1210 engages a separate slot 1314 on the exterior plates 1202, 1204 when adjacent exterior plates are joined together at right angles.

Figure 14B:
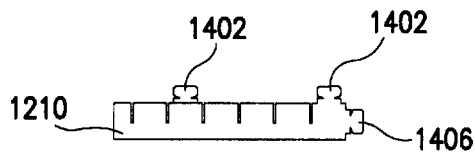
FIGS. 14A–14D are plan views of exemplary ribs for use in the second embodiment of FIG. 12.
Figure 14D:
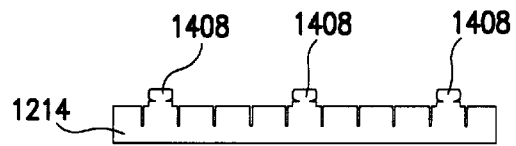
Figure 14A:
Figure 14C:
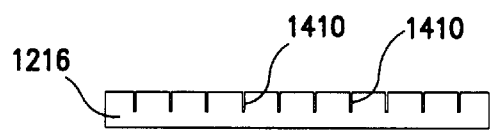

Turning to FIGS. 14C and 14D, the horizontal set of ribs 1504 is illustrated. The standard horizontal rib 1216 includes a plurality of slots 1410 that engage corresponding slots 1404 in the vertical ribs. The tabbed horizontal rib 1214 may include a plurality of tabs 1408 that engage corresponding slots 1314 in the interior plates.

Figure 15:
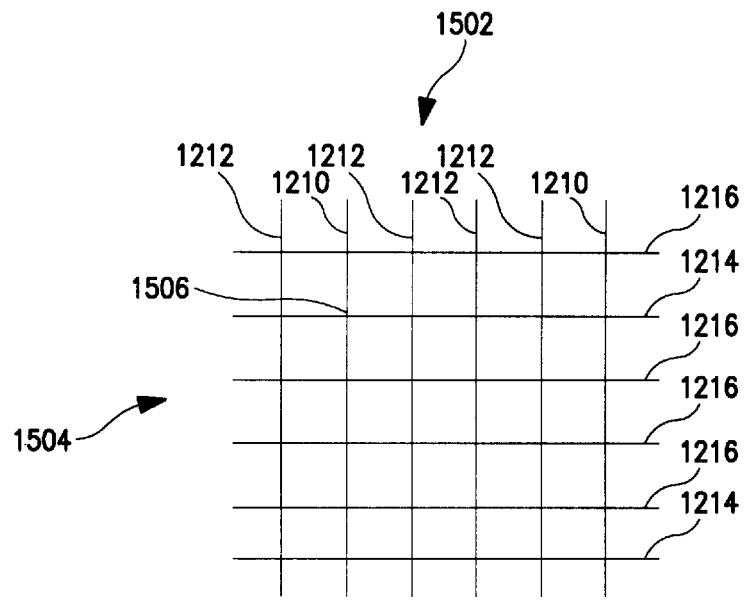
FIG. 15 is a plan view of a cell like rib structure for use in the second embodiment of FIG. 12.

Turning to FIG. 15, the horizontal ribs 1504 and the vertical ribs 1502 may be arranged orthogonal to form a square cell like structure. Those skilled in the art will recognize that other structures such as honeycomb structures may also be utilized without departing from the spirit and scope of the present invention.

The tabbed horizontal rib 1214 is arranged periodically among the standard horizontal ribs 1216 so that its tabs 1408 properly engage slots 1314 in the interior plates. Similarly, the tabbed vertical rib 1210 is periodically arranged among the standard vertical ribs 1212.

Advantageously, the entire housing structure may be assembled with slot-to-slot joints and tab-to-slot joints as earlier described. Again, generally the horizontal ribs 1504 and the vertical ribs 1502 engage each other in slot-to-slot joints 1506, while the exterior and interior plates are joined to the cell like structure via tab-to-slot joints. The joints may be brazed through techniques known to those skilled in the art.

The embodiments that have been described herein, however, are but some of the several which utilize this invention and are set forth here by way of illustration but not of limitation. It is obvious that many other embodiments, which will be readily apparent to those skilled in the art, may be made without departing materially from the spirit and scope of the invention as defined in the appended claims.

What is claimed is:

1. A flow through drum structure comprising:
   at least two annular metallic members;
   a plurality of metallic ribs disposed between said annular metallic members and coupled to said annular members via associated joints, at least one of said joints comprising:
     a first opening defined by portions of at least one of said annular members, said first opening comprising a body portion and an extending portion; and
     a second opening defined by portions of at least one of said rib members, said at least one rib member having a portion disposed in said extending portion of said first opening with said second opening at least partially overlapping said body portion to define a joined opening between said at least one annular member and said at least one rib member.

2. A flow through structure according to claim 1, wherein said first opening has a plurality of body portions at least partially overlapping a corresponding plurality of second openings in said second member to define a plurality of joined openings.

3. A flow through structure according to claim 2, wherein said plurality of body portions and said corresponding plurality of second openings completely overlap.

4. A flow through structure according to claim 1, wherein said body portion of said first opening is substantially rectangular.

5. A flow through structure according to claim 1, said structure further comprising a bonding agent disposed in said joined opening.

6. A flow through structure according to claim 5, wherein said bonding agent is adhesive.

7. A flow through structure according to claim 1, said structure comprising first and second outer ones of said annular metallic members, and first and second inner ones of said annular metallic members disposed between said first and second outer members.

8. A flow through structure according to claim 7, wherein said ribs extend between said first and second outer annular metallic members.

9. A flow through structure according to claim 7, wherein said ribs are coupled to each of said inner and outer annular metallic members by said associated joints.

10. A flow through structure according to claim 1, said structure further comprising a screen coupled to an outside scalloped edge of said at least two annular members and said plurality of metallic ribs.

* * * * *